United States Patent
Landis et al.

(10) Patent No.: US 6,214,609 B1
(45) Date of Patent: *Apr. 10, 2001

(54) METHOD AND APPARATUS FOR PREPARATION OF CHIRAL BETA AMINO ACIDS USING PENICILLN G ACYLASE

(75) Inventors: Bryan H. Landis, Manchester, MO (US); John S. Ng, Chicago, IL (US); Ravindra S. Topgi, Palatine, IL (US); Edward E. Yonan, Carol Stream, IL (US); Ping T. Wang, Manchester, MO (US)

(73) Assignee: Monsanto Company, Skokie, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/071,620

(22) Filed: May 1, 1998

Related U.S. Application Data (60) Provisional application No. 60/045,454, filed on May 1, 1997.

(51) Int. Cl.[7] ............................. C12P 13/04; C07C 1/04

(52) U.S. Cl. .......................................... 435/280; 435/106

(58) Field of Search ................................. 435/280, 106

(56) References Cited

U.S. PATENT DOCUMENTS

| | | | |
|---|---|---|---|
| 5,057,607 | * 10/1991 | Zmijewski, Jr. et al. | 540/364 |
| 5,728,876 | * 3/1998 | Balkenhohl et al. | 564/136 |
| 5,840,961 | * 11/1998 | Behling et al. | 560/172 |

FOREIGN PATENT DOCUMENTS

| | | |
|---|---|---|
| WO 8901047 | 2/1989 | (WO) . |
| 9402628 | 2/1994 | (WO) . |

OTHER PUBLICATIONS

Didziapetris et al., "Penicillin acylase–catylyzed acyl group transfer to amino acids, their esters and peptides: a kinetic study", Biomed. Biochem. Acta 50 (10/11) : S 237–S 242 (1991).*

Rossi et al., "THe use of benzylpenicillinacylase from *Escherichi coli* in the resolution of some racemic beta, gamma, delta and epsilon–amino acids", Experientia 33 (12) : 1557–9 (1977).*

Soloshonok et al., "Biocatalytic approach to enantiomerically pure beta amino acids", Tetrahedron: Asymmetry 6 (7) : 1601–10 (1995).*

K. Takahashi et al., Chem. Abstracts, vol. 111(7), Abs. No. 53495 (1989).

Cardillo et al., J. Org. Chem., vol. 61, (24) pp. 8651–8654 (1996).

Soloshonok et al., Tetrahedron Asymm., vol. 5(6) pp. 1119–1126 (1994).

Soloshonok et al., Tetrahedron Asymm., vol. 5(7) pp. 1225–1228 (1994).

Didziapetris et al., FEBS Letters, vol. 287 (1/2) pp. 31–33 (1991).

D.K. Roper and E.N. Lightfoot, Journal of Chromatography A, vol. 702, pp. 3–26 (1995).

M.A. Sanz et al., Journal of Chromatograhy A, vol. 719, pp. 195–201 (1996).

* cited by examiner

*Primary Examiner*—Sandra E. Saucier
(74) *Attorney, Agent, or Firm*—Fitzpatrick Cella Harper & Scinto (57) ABSTRACT

A method for preparing a chiral beta amino acid or its corresponding esters which comprises contacting a racemic beta amino acid, an acyl donor and Penicillin G acylase enzyme under conditions appropriate to stereoselectively acylate one enantiomer of the racemic beta amino acid to its corresponding N-acylated derivative whereby the opposite enantiomer of the beta amino acid is retained in enantiomerically enriched form.

17 Claims, 1 Drawing Sheet

Figure 1

METHOD AND APPARATUS FOR PREPARATION OF CHIRAL BETA AMINO ACIDS USING PENICILLN G ACYLASE

This application claims the benefit of U.S. Provisional application No. 60/045,454 filed May 1, 1997.

BACKGROUND OF THE INVENTION

1. Field of the Invention

This invention generally relates to enzyme catalyzed processes for producing chiral β-amino acids. In particular, this invention relates to processes for producing chiral β-amino acids employing Penicillin G acylase.

2. Related Background Art

The current evolving regulatory climate in the development of chiral drugs has created the necessity of preparing highly optically active compounds in pharmaceutical, agricultural and chemical industries. This development has presented many opportunities to synthetic chemists who are interested in the development of new chirotechnology. In recent years there have been explosive advances in the development of new synthetic methods, including asymmetric syntheses, stereoselective crystallization, chiral chromatography, racemate resolution and catalytic kinetic resolution, to prepare optically pure compounds. Despite these new developments, there are still relatively few efficient scalable chirotechnologies capable of producing multikilogram to ton quantities of optically active compounds economically.

Enzyme-catalyzed syntheses have been used in the commercial production of chiral pharmaceuticals. We have developed a new process for the preparation of chiral β-amino acids or their corresponding esters using enzyme-catalyzed acylations or enzyme-catalyzed deacylations.

Penicillin G acylase is a serine hydrolase with a high specificity for the acyl side chain (phenylacetyl) but a low selectivity for the amino side chain (R. Didziapetris et al., (1991) FEBS Letters 287 (1,2), 31). The enzyme is comprised of two subunits, α and β, each of which may have activity (70% for the α, 30% for the β chain) (V. E. Kabakov et al., (1995) Biochemistry (Moscow) 60 (5), 593; I. Prieto et al. (1990), Appl. Microbiol. Biotechnol. 33, 553).

Penicillin G acylase has traditionally been used to hydrolyze penicillin G (See, for example, J. G. Shewale and H. Sivaraman, (1989) Process Biochemistry, August, 1989, 148; F. Ishimura and K. Suga, (1992) Biotechnol. Bioeng. 39 (2), 171; J. Bryjak et al., (1996) Enzyme And Microbial Technology 19, 196).

The use of acylases in the preparation of alpha amino acids is known (Greenstein, J. P.; Chemistry of the Amino Acids; Wiley: New York, 1961; Greenstein, J. P.; Method. Enzymol. 1957, 3, 554; Chibata, I; Method. Enzymol. 1976, 44, 554; Chenault, H. K.; J. Am. Chem. Soc. 1989, 111, 6354.). The use of Penicillin acylases in the resolution of gamma amino acids using enzymatic deacylation was reported in WO 94/02628. Enzymatic acylation was not reported in this work.

The use of Penicillin acylases in the resolution of beta amino acids using enzymatic deacylation has been reported (Soloshonok; SYNLETT, 1993, 339; Soloshonok; Tetrahedron Asymmetry, 1994, 5, 1119; Soloshonok; Tetrahedron Asymmetry, 1994, 5, 1225) However, enzymatic acylation was not reported in this work and the beta amino acids used for the deacylation do not contain any alkynyl or alkenyl functions, which are key beta amino acids leading to active anti-platelet drug candidates.

The use of Penicillin acylases in the acylation of beta lactam intermediates was reported in 1991 (Zmijewski, M. J.; Tetrahedron Letters, 1991, 32, 1621). No work on beta amino acids was reported in this work.

This invention is useful for preparing compounds that contain chiral beta amino acids or their derivatives. The chiral β-amino acids and their derivatives are useful for making pharmaceuticals, such as antiplatelet agents (Zablocki et al, J. Med. Chem., 1993, 36, 1811; Bovy et al, Bioorg. Med. Chem, 1994, 2, 881–895; Zablocki et al, J. Med. Chem., 1995, 38, 2378; U.S. Pat. No. 5,424,334; U.S. Pat. No. 5,481,021), immunological response modifiers (Suda et al, J. Antibiot., 1976, 29, 100), anti-hypertensive agents (Chaturvedi et al, J. Med. Chem., 1970, 13, 177; Lizuk at al, J. Chem. Soc., Chem. Commun., 1989, 1978; Okino et al., Tetrahedron Lett., 1993, 34, 501); and anticancer agents (Denis et al., J. Org. Chem., 1990, 55, 1957).

SUMMARY OF THE INVENTION

This invention provides a method for preparing a chiral beta amino acid which comprises contacting a racemic beta amino acid, an acyl donor and Penicillin G acylase enzyme under conditions appropriate to stereoselectively acylate one enantiomer of the racemic beta amino acid to its corresponding N-acylated derivative whereby the opposite enantiomer of the beta amino acid is retained in enantiomerically enriched form.

This invention also provides a method for preparing a chiral beta amino acid which comprises contacting a racemic amide with a Penicillin G acylase enzyme under conditions appropriate to stereoselectively deacylate one enantiomer of the racemic amide to its corresponding beta amino acid whereby the opposite enantiomer of the racemic amide is retained in enantiomerically enriched form.

This invention also provides an apparatus useful for preparing chiral beta amino acids comprising serially connected bath, pumping means, enzyme contacting means, a first chromatographic separation means, a second chromatographic separation means, and a third chromatographic means and an effluent directing means.

DETAILED DESCRIPTION

This invention provides a method for preparing a chiral beta amino acids which is generally depicted in Scheme 1:

Scheme 1
Enzymatic Acylation (A) + Acyl donor, Organic or Aqueous solvents, enzymes (e.g. Penicillin acylase) → (B) +

(C)

In Scheme 1 substrate A, a racemic β-amino acid or its corresponding ester, is reacted under aqueous or organic conditions with an acyl donor and Penicillin G acylase, whereby one enantiomer of the racemic amino acid stereoselectively reacts with the acyl donor producing a chiral amide, compound "B", and the other enantiomer remains predominantly unreacted as the chiral amino acid, compound "C". As described herein, compounds B and C are easily separated to enable production enantiomerically enriched β-amino acids. The enzyme Penicillin G acylase stereoselectively acylates the R-isomer of the racemic amino acid substrate under these reaction conditions.

In the acylation process of the invention, the racemic β-amino acid and corresponding esters include compounds wherein $R_1$ comprises substituted or unsubstituted alkyl, alkenyl, alkynyl, aryl, carboxyl derivatives, haloalkyl, and monocyclic heterocycles, optionally substituted with alkyl, halogen, haloalkyl, cyano, hydroxy, aryl, fused aryl, nitro, alkoxy, aryloxy, alkylsulfonyl, arylsulfonyl, sulfonamide, thio, alkylthio, carboxyl derivatives, amino, and amido. $R_2$ comprises hydrogen, substituted or unsubstituted alkyl, alkenyl, alkynyl, haloalkyl, aryl, arylalkyl, sugars, steroids and, in the case of the free acid, all pharmaceutically acceptable salts thereof.

As used herein, the term "acyl donor" is intended to comprise compounds having the structure:

wherein $R_3$ comprises phenyl, phenoxy, amino, phenyl glyconyl, 4-methylphenyl, 4-methoxy phenyl, p-nitro phenyl, 2-pyridyl, 3 pyridyl and 4-pyridyl. Optionally substituted, $R_4$ comprises hydroxy; alkoxy, wherein "alkoxy" includes, but is not limited to, ethoxy, methoxy, butoxy, 2-chloroethoxy, trichloroethoxy, trifluoroethoxy, cyanomethoxy, vinyloxy, substituted vinyloxy, aretyloxy, and phenacetyloxy; alkyl; alkenyl; alkynyl; haloalkyl; anyl; anylalkyl; sugars or steroids.

Three preferred acyl donors, which are commercially available, are methyl phenoxyacetate, methyl phenylacetate and phenylacetic acid. As discussed herein, the most preferred acyl donor is phenyl acetic acid, where $R_3$ is phenyl acetyl and $R_4$ is hydroxyl. This acyl donor offers many advantages in the invention, most important of which is removing the need to purify the starting material racemic amines. The phenyl acetic acid forms a highly pure salt with the racemic amines and thereby purifies the amines in this salt formation process before enzymatic resolution.

Thus the invention also provides a method for preparing a chiral beta amino acid or its corresponding ester which comprises:
(a) dissolving a racemic beta amino acid or its corresponding ester in phenyl acetic acid to form a salt of the racemic beta amino acid and phenylacetic acid;
(b) dissolving the salt formed in (a) with an aqueous solvent; and
(c) adding Penicillin G acylase enzyme to the aqueous solution from (b) under conditions appropriate to stereoselectively acylate one enantiomer of the racemic beta amino acid to its corresponding N-acylated derivative leaving the opposite enantiomer of the beta amino acid substantially unreacted.

In the practice of this method, formation of the salt can be facilitated by addition of organic solvents such as those discussed herein as organic co-solvents. Particularly preferred among these is hexanes.

This invention also provides a method for preparing a chiral beta amino acid which is generally depicted in Scheme 2:

In Scheme 2, the substrate compound "D" is reacted under aqueous or organic conditions with Penicillin G acylase, whereby one enantiomer of the racemic amide stereoselectively deacylates producing a chiral β-amino acid or its corresponding ester, compound "E", and the other enantiomer remains unreacted as the chiral amide, compound "F". As described herein, compounds E and F are easily separated to enable production of enantiomerically enriched β-amino acids. The rate of deacylation of S-amide by Penicillin G acylase is significantly slower than the corresponding R-amide, and this difference allows one to selectively deacylate the R-amide to form the β-amino acid enriched in the R-enantiomer. However, this rate can be enhanced by using a large excess of the enzyme Penicillin G acylase, longer reaction time and higher temperature. Such enhanced conditions could be used, for example, to prepare β-amino acid enriched in the S-enantiomer from the S-amide, compound "F", which has been separated from the R-amino acid, compound "E".

In the deacylation process of the invention, the racemic amide of the β-amino acid or corresponding ester include compounds wherein $R_1$ can comprise alkyl; alkenyl; alkynyl; aryl; carboxyl derivatives; haloalkyl; monocyclic heterocycles; monocyclic heterocycles optionally substituted with alkyl, halogen, haloalkyl, cyano, hydroxy, aryl, fused aryl, nitro, alkoxy, aryloxy, alkylsulfonyl, arylsulfonyl, sulfonamide, thio, alkylthio, carboxyl derivatives, amino, amido; $R_2$ comprises hydrogen; substituted and alkyl; alkenyl; alkynyl; haloalkyl; aryl; arylalkyl; sugars; steroids and in the case of the free acid, all pharmaceutically acceptable salts thereof; and $R_3$ comprises substituted or unsubstituted phenyl, phenoxy, amino, phenyl glyconyl, 4-methylphenyl, 4-methoxy phenyl, p-nitro phenyl, 2-pyridyl, 3 pyridyl and 4-pyridyl. In a preferred embodiment the substrate has a structure wherein $R_1$ is substituted or unsubstituted alkenyl or alkynyl.

The amide substrate from Scheme 2, compound D, can be prepared by methods known to those of ordinary skill in the art. For example, the corresponding racemic amine of the desired amide is reacted with one of the "acyl donors" described above, for example phenylacetyl chloride, in the presence of a base, for example triethylamine, at room temperature for approximately 2 hours, to give the desired amide.

In the processes of the invention the alkyl substituents can be optionally substituted with halo, haloalkyl, hydroxy, alkoxy, aryloxy, thio, alkylthio, arylthio, alkysulfoxide, alkylsulfonyl, arylsulfoxide, arylsulfonyl, cyano, nitro, amino, alkylamino, dialkylamino, alkylsulfonamide, arylsulfonamide, acylamide, carboxyl derivatives, sulfonamide, sulfonic acid, phosphonic acid derivatives, phosphinic acid derivatives, aryl, arylthio, arylsulfoxide, or arylsulfone all optionally substituted on the aryl ring with halo, haloalkyl, cyano, nitro, hydroxy, carboxyl derivatives, alkoxy, aryloxy, amino, alkylamino, dialkylamino, amido, aryl, fused aryl, monocyclic heterocycles; and fused monocyclic heterocycles, monocyclic heterocyclicthio, monocyclic heterocyclicsulfoxide, and monocyclic heterocyclic sulfone, which can be optionally substituted with halo, haloalkyl, nitro, hydroxy, alkoxy, fused aryl, or alkyl.

In the processes of the invention the aryl substituent can be optionally substituted in one or more positions with halo, haloalkyl, alkyl, alkoxy, aryloxy, methylenedioxy, ethylenedioxy, alkylthio, haloalkylthio, thio, hydroxy, cyano, nitro, carboxyl derivatives, amido, acylamino, amino, alkylamino, dialkylamino, trifluoroalkoxy, trifluourmethylsulfonyl, alkylsulfonyl, sulfonic acid, sulfonamide, aryl, fused aryl, monocyclic heterocycles and fused monocyclic heterocycles.

As used herein, alkyl, alkenyl and alkynyl groups, whether as substituents themselves or as portions of substituents, are $C_1$–$C_{50}$, with $C_1$–$C_{20}$ preferred and $C_1$–$C_{10}$ most preferred. As used herein, "carboxyl derivatives" includes carboxylic acids, carboxylic esters and carboxylic amides. As used herein, "halogen" and "halo" portions of substituents include Cl, F, Br, and I.

As used herein, "fused aryl" substituents include, but are not limited to, Pentalene, Indene, Naphthalene, Azulene, Heptalene, Biphenylene, asymm-Indacene, symm-Indacene, Acenaphthylene, Flourene, Phenalene, Phenanthrene, Anthracene, Flouranthene, Acephenanthrylene, Aceanthrylene, Triphenylene, Pyrene, Chrysene, Naphthacene, Plejadene, Picene, Perylene, Pentaphene, Pentacene, Tetraphenylene, Hexaphene, Hexacene, Rubicene, Coronene, Trinaphthylene, Heptaphene, Heptacene, Pyranthrene, Ovalene, Indane, Acenaphthene, Cholanthrene, Aceanthrene, Acephenanthrene., Violanthrene, Isovialanthrene, As used herein "monocyclic heterocycle" substituents include but are not limited to Furane, Imidazole, Pyrazole, Pyridine, Pyrazine, Pyrimidine, Pyridazine, Thiophene, Tellurophene, Selenophene, Pyrane, and Pyrrole. As used herein "fused monocyclic heterocycle" substituents include but are not limited to Pyrrolizine, Indolizine, Isoindole, 3H-Indole, Indole, 1H-Indazole, Purine, 4H-Quinolizine, Isoquinoline, Quinoline, Phthalazine, 1,8-Naphthyridine, Quinoxaline, Quinazoline, Quinoline, Pteridine, 4aH-Carbazole, Carbazole, β-Carboline, Phenanthridine, Acridine, Perimidine, 1,7-Phenanthroline, Phenazine, Phenomercazine, Phenarsazine, Isothiazole, Phenophosphazine, Phenotellurazine, Phenoselenazine, Phenothiazine, Isoxazole, Furazane, Phenoxazine, Isochromane, Chromane, Pyrrolidine, Pyrroline, Imidazolidine, Phenomercurine, Isoarsindole, Arsindole, Isoarsinoline, Arsinoline, Arsanthridine, Arcidarsine, Arsanthrene, Isophosphindole, Phosphindole, Isophosphinoline, Phosphinoline, Phosphanthrene, Selenanthrene, Benzo[b]thiophene, Naphthol[2,3-b] thiophene, Thianthrene, Phenothiarsine, Isobenzofurane, 2H-Chromene, Xanthene, Phenoxantimonine, Phenoxarsine, Phenoxaphosphine, Phenoxatellurine, Phenoxaselenin, and Phenoxathiine.

As used herein "sugar" includes the monosaccharides glyceraldehyde, erythrose, threose, ribose, arabinose xylose, lyxose, allose, altrose, glucose, mannose, gulose, idose, talose, galactose, psicose, fructose, sorbose, tagatose, ribulose, xylulose, erythrulose, dihydroxyacetone, and oligosaccharides based thereon, including but not limited to sucrose, trehalose, maltose, cellobiose, gentiobiose, lactose, and raffinose. As used herein "steroids" refers to compounds based on the compound sterane (perhydro-1H-cyclopenta[a] phenanthrene), including but not limited to gonane, estrane, andostane, pregnane, cholane, cholestane, ergostane, stigmastane, and derivatives thereof. As used herein, the terms "amino acid" and "amine", whether substrate or product, are synonymous and include their corresponding esters defined above. As used herein the terms "N-acylated amine derivative" and "amide" are synonymous.

Trimethyl silyl ("TMS") derivatives of the amino acids disclosed above can also be used in the reaction. TMS derivatives are preferred in the acylating reaction since the TMS group would enhance the precipitation of the R-amide from aqueous solution. Thus, in the enzymatic acylation method $R_1$ of the substrate can also contain the trimethylsilyl function.

Desilylation of TMS derivatives produced by the reactions can then be accomplished by standard methods known by those skilled in the art, for example, by dilution with ethanol and reacting with sodium ethoxide for approximately 1 hour at room temperature.

The enzyme Penicillin G acylase, also known as "PGA", "E.C. 3.5.1.11", "penicillin G amidase" or "penicillin amidohydrolase", has been used in the industrial production of 6-aminopenicillanic acid for the pharmaceutical industry. Penicillin G acylase can be derived from microorganisms belonging to the genera Acetobacter, Xanthomonas, Mycoplana, Protaminobacter, Aeromonas, Pseudomonas, Flavobacterium, Aphanocladium, and Cephalosporium by techniques known to those of ordinary skill in the art (K. Balasingham, D. Warburton, P. Dunnill, M. D. Lilly (1972), Biochim.Biophys. Acta 2276(1): 250–256. "Isolation and kinetics of penicillin amidase from *Escherichia coli.*", page 9, line 19).

In a preferred embodiment, the enzyme is derived from expressing the enzyme in *E. Coli*. Those of ordinary skill recognize that each enzyme is active in a certain pH range between 3 and 8.5, most preferably 6 to 8. A particular enzyme may show different activity as well as selectivity toward R and S enantiomers depending on the reaction conditions, which can be determined by those of ordinary skill in the art without undue experimentation using standard methods for determining enzyme activity and enantiomeric selectivity using chiral stationary phase high performance liquid chromatography methods.

The enzyme can be employed in the form of whole cells containing the enzyme, or extracts thereof or purified enzyme or enzyme fractions. Each form can be used as a solubilized form of enzyme or can be immobilized if desired. Immobilization methods which may be used in the practice of this invention include well known methods such as entrapment in polymeric gels, or attachment to solid supports by covalent attachment, crosslinking, adsorption, and encapsulation. Immobilization supports useful in the practice of this invention include, but are not limited to, porous glass and porous ceramics, bentonite, diatomaceous earth, charcoal Sepharose® and Sepharose® derivatives (Pharmacia Fine Chemicals, Uppsala Sweden), cellulose and cellulose derivatives, polyacrylamide and polyacrylamide derivatives, polyazetidine, alginate, and carrageenan.

Commercial sources also exist for both solubilized or immobilized forms of penicillin G acylase enzyme useful in the practice of this invention, including Calbiochem (e.g., "Penicillin Acylase", soluble enzyme Calbiochem-Novabiochem Corporation, 10394 Pacific Center Court, San Diego, Calif., 92121) Rohm-Pharma (e.g., "Eupergit Penicillin Acylase-600", immobilized enzyme Rohm GmbH, Chemische Fabrik, D-64275 Darmstadt, Germany), and Boehringer-Mannheim (e.g., "Penicillin-G-amidase-450" (e.g., "Penicillin -G-amidase-450", immobilized enzyme, and soluble enzyme) Sandhofer Strass 116, D-68298 Mannheim, Germany; Recordati (immobilized enzyme), 20060 Cassina De'Pecchi (Milano), Italy., immobilized enzyme) [Calibiochem-Novabiochem Corporation, 10394 Pacific Center Court, San Diego, Calif. 92121, Rohm GmbH, Chemische Fabrik, D-64275 Darmstadt, Germany, Sandhofer Strass 116, D-68298 Mannheim, Germany; Recordati (immobilized enzyme), 20060 Cassina De'Pecchi (Milano), Italy. Penicillin G acylase from different sources might show different activity as well as selectivity toward R- and S-enantiomers. The activity as well as selectivity depends on purity of the enzyme, temperature, pH, solvent and concentration of reactants.

In the practice of the stereoselective acylation method of the invention the ratio of units of enzyme ("u") to grams of substrate ("g") to grams of acylating agent ("g") is typically in the range of 1500 u:25 g:13 g to 7000 u:50 g:38 g. In a preferred embodiment, the ratio is 3750 u:37.5 g:24.5 g. In the practice of the stereoselective deacylation method of the invention the ratio of enzyme to substrate is typically in the range of 1500 u:25 g to 7000 u:50 g. In a preferred embodiment, the ratio is 3750 u:37.5 g.

Although the enzyme Penicillin G acylase prefers an aqueous environment, it can tolerate a certain percentage of organic co-solvent. Thus the reaction can be run under "aqueous conditions", meaning without organic co-solvent, or "organic conditions", meaning with organic co-solvent. The solubility of the substrate is important in enzyme catalyzed reactions to facilitate contact with the enzyme's reaction cavity. In order to obtain a homogeneous solution, a certain amount of organic co-solvent can be used in the process. Co-solvents are known to those of ordinary skill in the art and include solvents such as hexane, acetone, tetrahydrofuran ("THF"), dimethylformamide ("DMF"), acetonitrile, isopropanol, methanol, and toluene. Acetonitrile and methanol are the preferred co-solvents for the deacylation process. If a co-solvent is used, it is typically present to no more than 30% (v/v), preferably about 5% (v/v). However, recovery of unused starting material and processing of the aqueous phase to isolate the free amine is relatively easier if the reaction is performed without organic co-solvent.

Phosphate buffer is known to enhance the activity of the enzyme Penicillin G acylase. Thus, in the practice of the invention, a phosphate buffer concentration up to 1.0 M can be used. The enzyme exhibits higher activity in phosphate buffer around pH 8.0.

The process of this invention can be carried out at a pH ranging from about 3 to about 8. The transition period between deacylation and acylation lies between pH 6 and 6.5. Although pH 3.5 ensures total solubility of the amine in water, pH 6 is preferred.

The transition between deacylation and acylation is governed mostly by pH and, to a far less extent, by temperature.

In the practice of the invention, since the enzyme is selective for the R-isomer, selective acylation of the R-enantiomer occurs in the acylation reaction and selective deacylation of the R-enantiomer in the deacylation reaction. The processes of the invention, therefore, provide methods for obtaining substantially pure chiral β-amino acids. However, it is intended that use of the processes to obtain less than substantially pure compounds, i.e., mixtures which are "enantiomerically enriched" in one enantiomer, are within the scope of the invention. Monitoring the reaction to prevent more than 50% conversion of the substrate is important to maintain high optical purity of product. Progress of the enzymatic reaction and the 50% consumption point can be determined by methods known to those of ordinary skill in the art. Two such methods, base titration and HPLC, are preferred.

In a typical base titration method, as the enzyme cleaves, for example, the phenylacyl group, phenylacetic acid is formed as a by-product of deacylation. This acid lowers the pH of the reaction medium. In this event, a base, such as NaOH or $NH_4OH$, is added to maintain the starting pH. Consumption of the base equivalent to 50% of the starting material indicates 50% conversion point.

Reverse phase HPLC ("RP-HPLC") monitoring can be accomplished by calculating the area of the peak corresponding to the quantity of the racemic mixture, which allows one to draw a calibration curve. From the correlation plot, the quantity of the substrate left in the reaction mixture can be calculated. As an example, the following reverse phase conditions can be used to monitor the reaction:

i) column: Vydac-$C_{18}$ analytical (Vydac Separations Group, Hesperia, Calif.);
ii) solvents: Acetonitrile (0.1% Triethylamine) and Water (0.05% phosphoric acid);
iii) detection: 245 nm;
iv) flow rate: 1.25 mL per minute.

HPLC on chiral stationary phase ("chiral HPLC") can be used to separate R and S enantiomers, and thus can also be used to monitor the reaction. As an example, the following chiral HPLC conditions can be used to monitor the reaction:

i) column: (S,S) Whelk-O Chiral column (25×4.6 mm) (Regis Technologies, Inc., Morton Grove, Ill.);
ii) solvent system: Isopropanol: Hexane (30:70);
iii) detection: 245 nm;
iv) flow rate: 1.25 mL per minute.

In instances where the free amine lacks a strong chromophore to allow for separation of enantiomers monitoring of the reaction by detection of amines is hindered. Derivatization using methods known to those of ordinary skill in the art, such as with 1-Naphthoyl chloride, will provide for separation using chiral HPLC.

The product can be isolated by methods known to those of ordinary skill in the art. The amide is a solid whereas the amine is liquid. Hence filtration would be adequate to separate amide from amine. Further, any amine adhered to the surface of the amide can be extracted, for example, by washing with dilute acid.

Thereafter, the amines present in aqueous phase can be isolated and quantified in a number of ways. Two methods, ion-exchange chromatography and acid base extraction are preferred.

In the practice of ion-exchange chromatography the aqueous reaction mixture is passed over an acidic ion-exchange resin, for example Dowex 50× H (Aldrich), which retains the amine. The amine anchored on the ion exchange resin can then be recovered by eluting with solvent, for example, methanol containing ammonia.

The acid-base extraction approach is based on the finding that at pH levels above 7.5, the R- and S-amines are practically insoluble in water. Organic solvents can be used to extract these free amines from the aqueous reaction medium. At pH less than 8 the ethyl ester functionality seems to be stable as hydrolysis of the ester was not observed during work-up of the reaction mixture. In a preferred embodiment of the invention, the products are recovered by acid base extraction at a pH of between 7.5 and 8.

Figure 1:
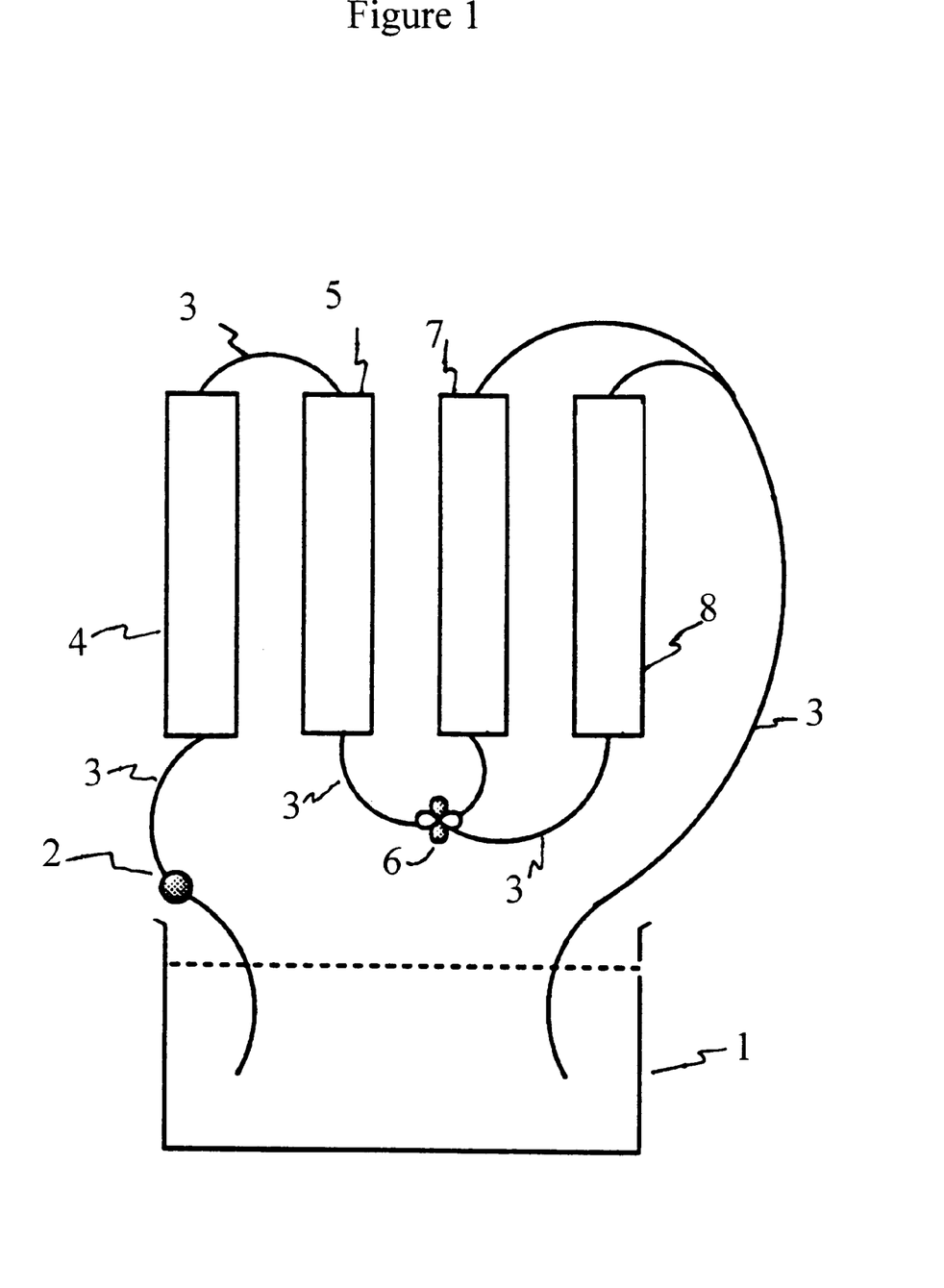
FIG. 1—Schematic representation of a preferred embodiment of an apparatus useful for performing a continuous enzymatic deacylation process according to the invention.

This invention also provides an apparatus useful for the stereoselective deacylation of a racemic mixture of amides to produce enantiomerically enriched amino acids. Deacylation of racemic amides may be carried out in a batch-wise manner using standard reactors such as round bottom flasks, fermenters or regular batch reactors. Alternately, a continuous process could be used. The apparatus of the invention, which is generally depicted in FIG. 1, comprises serially connected bath, pumping means, enzyme contacting means, a first chromatographic separation means, a second chromatographic separation means, and a third chromatographic means and an effluent directing means. As depicted in FIG. 1, the bath 1 comprises the reaction medium and the substrate, which can be in the form of a slurry. A pump means 2 draws the reaction medium through a fluid conducting means 3, for example tubing, and delivers to an enzyme contacting means 4, which generally comprises an enzyme immobilized on a substrate. Substrates and methods of enzyme immobilization are described above. As the reaction medium contacts the enzyme contacting means 4, the enzyme cleaves preferentially the R-isomer to produce an effluent containing the racemic mixture, the phenylacetic acid, the S-isomer and the R-amine. This effluent is then passed through the first chromatographic separating means 5, for example a basic ion exchange column, which retains the phenylacetic acid and produces a second effluent comprising the racemic mixture, the S-amide and the R-amine. This second effluent is then passed through the effluent directing means 6, such as a valve, and loaded on the second chromatographic means 7, for example an acidic ion-exchange column, where the R-amine is retained and a third effluent is produced comprising the racemic mixture and the S-amide. This third effluent is then returned to the bath 1 to complete one cycle and then taken up by the pumping means 2 through the fluid conducting means 3 to begin the next cycle. This apparatus, operating in a continuous process and repeated for several cycles, will consume the racemic mixture leaving only the S-amide in the bath.

Once the required enantiomeric enrichment is attained, the effluent directing means 6 is manipulated to direct the third effluent to a third chromatographic means 8, for example a second acidic ion-exchange column, where the S-amine, formed by reaction of the enzyme on the reaction medium now enriched in the S-amide, will be retained. At the end of the process the second chromatographic means 7 contains the R-amine and the third chromatographic means 8 contains the S-amine. Simple washing of these chromatographic means will liberate the free amines.

The following examples, which further illustrate this invention, are not intended, and should not be interpreted, to limit the scope of the invention defined in the claims which follow thereafter.

In the Examples, the following HPLC conditions were used:

a) RP-HPLC:
  i) column: Vydac-$C_{18}$ analytical (Vydac Separations Group, Hesperia, Calif.);
  ii) solvents: Acetonitrile (0.1% Triethylamine) and Water (0.05% phosphoric acid);
  iii) detection: 245 nm;
  iv) flow rate: 1.25 mL per minute.

b) Chiral HPLC:
  i) column: (S,S) Whelk-O Chiral column (25×4.6 mm) (Regis Technologies, Inc., Morton Grove, Ill.);
  ii) solvent system: Isopropanol: Hexane (30:70);
  iii) detection: 245 nm;
  iv) flow rate: 1.25 mL per minute.

EXAMPLE 1

Enzymatic Acylation (I)

A) (±) Ethyl 3-amino-5-(trimethylsilyl)-4-Pentynoate (500 mg) was added dropwise to dilute hydrochloric acid (50 mL, pH 1.9) with stirring. After 10 minutes, the insoluble material was extracted using t-butyl methyl ether (25 mL). The layers were separated and the pH of the aqueous phase was adjusted to 6 using ammonium hydroxide (2.5 N). Phenylacetic acid (2 equiv.) was added and the mixture was stirred for an additional 10 minutes. The pH was adjusted to 6 using dilute ammonium hydroxide and the mixture was stirred for about 10 minutes. Enzyme penicillin G acylase (250 Units, Boehringer Mannheim, soluble form) was added and the mixture was stirred at room temperature for 42 hours. The pH of the reaction mixture was adjusted to 4.0 using dilute hydrochloric acid and stirring was continued for 10 minutes. The product was collected by filtration and washed with water (pH 4.0 10 mL; sterile 10 mL). The washings were added to the main filtrate.

The residue was dissolved in ethyl acetate (25 mL) and back extracted with water (pH 8.3, 2×15 mL). The ethyl acetate phase was dried over sodium sulfate and evaporated to dryness in under vacuum. One milligram of this material was dissolved in isopropanol (1 mL) and an aliquot (25 µL) was analyzed on a chiral HPLC column.

The filtrate along with the washings were treated with ammonium hydroxide (2.5 N) to obtain pH 8.2 and the basic phase was extracted with ethyl acetate (2×25 mL). The organic phase was dried over sodium sulfate and evaporated to dryness under vacuum (bath temperature 55° C.). The material was then dissolved in ethyl acetate (50 mL). An aliquot (5 mL) was treated with triethylamine (4 drops) and 1-naphthoyl chloride (25 µL) and stirred for approximately 5 minutes. Additional 1-naphthoyl chloride (25 µL) was added and stirred at room temperature for 2 hours. An aliquot (1 uL) was injected on the chiral HPLC column. Results indicated the product contained the desired silylated amine in an R:S ratio of 2:98.

Quantification from calibration curves indicated 165 mg of the undesired silylated R-amine and 145 mg of the desired silylated S-amine. In addition, approximately 30% more of the desired S-amine was obtained in the desilylated form. It is likely that desilylation occurred as a result of the basic work up (pH 8.2) after the enzymatic reaction.

B) 11 g Scale. The free amine (11 g) was added dropwise to dilute hydrochloric acid (960 mL, pH 1.76) with stirring. After pH was adjusted to 2 using dilute hydrochloric acid and stirred for 15 minutes, the solution was transferred to a separating funnel. The insoluble material was extracted using t-butyl methyl ether (200 mL). The layers were separated and the pH of the aqueous phase was adjusted to 6 using ammonium hydroxide (2.5 N). Phenylacetic acid (20 g in 40 mL water, pH adjusted to 6) was added and the mixture was stirred for 15 minutes. The pH was adjusted to 6 using dilute ammonium hydroxide and the mixture was stirred for another 15 minutes. Penicillin G acylase enzyme (1760 Units, Boehringer-Mannheim, soluble form) was added and the mixture was stirred at room temperature for 52 hours. When no precipitate was observed, more enzyme (1700 Units) was added and stirred at room temperature for about 24 h. When no precipitate was observed again, the reaction flask was connected to vacuum and stirred at room temperature for about 4 hours. Formation of the precipitate was observed. After disconnecting the vacuum, the pH of the reaction mixture was adjusted to 4.0 using dilute HCl. This solution was stirred for 15 minutes and the product was collected by filtration. The product was washed with water (pH 4.0, 25 mL and sterile 25 mL). The washings were added to the main filtrate.

The residue was dissolved in ethyl acetate (150 mL) and water (pH 8.0, 200 mL) was added. The two phases were transferred to a separating funnel. After vigorous agitation the two layers were allowed to separate. There was no clear separation of the layers, and more ethyl acetate (200 mL) was added to facilitate clear phase separation. The ethyl acetate phase was dried over sodium sulfate and evaporation to dryness in vacuo gave a solid material (9.84 g). A portion of this material (50 mg) was dissolved in isopropanol (5 mL) and an aliquot (3 µL) was analyzed on a chiral HPLC column for amides formed.

The filtrate and the washings were treated with ammonium hydroxide (2.5 N) to obtain pH 8.1 and the basic phase was extracted with ethyl acetate (2×400 mL). The organic phase was dried over sodium sulfate and evaporated to dryness under vacuum (bath temperature 55° C.). The oily product weighed 4.67 g. An aliquot of this material (7 mg) dissolved in ethyl acetate (5 mL) was treated with triethylamine (4 drops) and 1-naphthoyl chloride (50 µL). After 16 hours reaction at room temperature, an aliquot (5 µL) was injected on a chiral HPLC column. Results indicated the product contained the desired silylated amine in an R:S ratio of 2:98. Quantification from calibration curves indicated 3.85 g of the R-amine and 2.70 g of the S-amine.

C) Enzymatic acylation using immobilized enzyme. Dilute hydrochloric acid (pH 2, 60 mL) was added to racemic amine (600 mg) with stirring. After 10 minutes stirring, the pH was adjusted to 2 using dilute hydrochloric acid and the insoluble material was extracted with ethyl acetate (50 mL). The layers were separated and the pH of the aqueous phase was adjusted to 6 using ammonium hydroxide (2.5 N). Phenyl acetic acid (3 mL, 500 mg/mL, pH 6) was added and the mixture was stirred for about 10 minutes. The pH was adjusted to 6 using dilute ammonium hydroxide and the mixture was stirred for 10 minutes. Under vigorous stirring an aliquot (10 mL) was transferred to a reaction flask. Penicillin G acylase enzyme (36 Units, Boehringer-Mannheim, immobilized form) was added and the mixture was to stirred at room temperature. After 15 hours stirring the reaction flasks were placed in water bath (35° C.) and shaken at 400 rpm for about 4 hours. The solution was allowed to return to room temperature, dilute hydrochloric acid (10 mL, pH 2) was added, and the mixture was shaken at 350 rpm for another 10 minutes. After adjusting the pH to about 4.0 the reaction mixture was filtered and the product was washed with dilute hydrochloric acid (pH 2.0, 2×5 mL). The residue was dissolved in ethyl acetate (25 mL). After adding water (10 mL), the pH was raised to 7.8 using dilute ammonium hydroxide. The two phases were then transferred to a separating funnel. After vigorously agitation the two layers were separated and the aqueous phase was discarded. The ethyl acetate phase was dried over sodium sulfate and evaporated to dryness under vacuum (bath temperature 55° C.). This dry material was dissolved in isopropanol (5 mL) and an aliquot (5 μL) was analyzed for amides on the chiral HPLC column.

The pH of the preserved filtrate along with the washings was adjusted to pH 7.8 and the liberated amines were extracted with ethyl acetate (2×15 mL). The aqueous phase was discarded. The ethyl acetate extracts were combined and dried over sodium sulfate and evaporated to dryness on a rotary evaporator under reduced pressure (bath temperature 55° C.). The dried material was dissolved in ethyl acetate (50 mL) and an aliquot (5 mL) was treated with triethylamine (4 drops) and 1-naphthoyl chloride (40 μL). The reaction mixture was allowed to stir at room temperature. After 20 hours stirring at room temperature, the reaction flasks were stored in a refrigerator. Before analysis the reaction flasks were allowed to attain room temperature. An aliquot (5 μL) was analyzed on the chiral HPLC column. Results indicated the product contained the desired silylated amine in an R:S ratio of 2:98.

Quantification from calibration curves established using reference compounds on (S,S) Whelk-O chiral column indicated that 87 mg of R-amide and 29 mg of S-amine were obtained from 100 mg of starting racemic amine. In addition, approximately 30% of more desired S-amine was obtained in the desilylated form.

D) Enzymatic Acylation of Amine Phenyl Acetic Acid Salt.

1. Preparation phenyl acetic acid salt of racemic ethyl 3-amino-5-(trimethylsilyl)-4-pentynoate. Racemic ethyl 3-amino-5-(trimethylsilyl)-4-pentynoate (67 g) was reacted with 39 g of phenylacetic acid. The product was filtered and washed with hexane and dried in a vacuum oven to give 100 g the desired racemic ethyl 3-amino-5-(trimethylsilyl)-4-pentynoate phenyl acetic acid salt.

2. Enzymatic Acylation. The racemic ethyl 3-amino-5-(trimethylsilyl)-4-pentynoate phenyl acetic acid salt (82 g) was added to 1 liter of water, 14.5 g(345 Units/g) of immobilized Penicillin G Acylase (Boehringer Mannheim) was added and the reaction was maintained at 28° C. The reaction was monitored periodically until 98% of R-amine was consumed, then the reaction was quickly cooled to attain approximately 5° C. Ice cooled methyl t-butyl ether ("MTBE") (500 mL) was added and the pH was adjusted between 7.8 and 8.0 using ice cooled saturated $KHCO_3$. The organic extract was collected. The extraction was repeated twice using 300 mL ice cooled MTBE and all the organic extracts were combined. Under vigorous stirring and cooling, ice cooled 0.5 N HCl was added to combined organic extracts to obtain pH around 2.0. The contents were transferred to a separating funnel, agitated and the aqueous layer was separated. The extraction was repeated twice and the organic phase was preserved. The aqueous extracts were then combined, transfered to a separating funnel and washed with 250 mL MTBE. The washings were added to earlier organic phase and the aqueous phase was preserved.

The organic phase was washed with 200 mL water (pH 8.0) and with 200 mL brine. The washed organic phase was collected, dried over sodium sulphate, and evaporated to dryness (bath temp. 50° C., Vacuum: 27") to obtain amide. This amide was analyzed for R- and S-isomers. The desired (R)-amide was obtained in 48%. molar yield (theoretical yield: 50%) in 97% optical purity.

The preserved aqueous phase was cooled to approximately 5° C. Under vigorous stirring, ice cooled saturated $KHCO^3$ solution was added to attain pH of 7.9. The liberated amine was extracted with 500 mL ice cooled MTBE. The extraction was repeated using ice cooled MTBE (2×350 ml). The organic phase was collected, dried over sodium sulphate, and evaporated to dryness (bath temperature 50° C., vacuum: 27") to obtain the amine. This amine was analyzed for R- and S-isomers. The desired (s)-amine was obtained in 48.4% molar yield (theoretical yield:50%) in 99.3% optical purity.

EXAMPLE 2

Enzymatic Acylation of Ethyl 3-amino-4-pentynoate (L)

In water(30 mL) were mixed ethyl 3-amino-4-pentynoate hydrochloride (258.3 mg, 1.5 mmoles), 30.6 mg (3.95 units) immobilized penicillin G amidohydrolase [Rohm-Pharma] and ethyl phenylacetate (205.7 mg, 1.25 mmoles). The initial pH (3.48) was adjusted to pH 6 with N NaOH (0.5 N) before addition of the ethyl phenylacetate. After 3 hours, an additional 0.9 mmole ethyl phenylacetate was added. This suspension was stirred vigorously at room temperature for six hours. Periodically, 1 mL samples were taken and diluted with acetonitrile and analyzed by reversed phase HPLC.

After 6 hours, the bioconversion suspension (25 mL) was extracted twice with diethyl ether (25 mL, pH 6 ether extracts). The pH of the aqueous layer was then raised to 8.1 with $NaHCO_3$ (0.72 g) and was extracted twice with diethyl ether (25 mL, pH 8 ether extracts). Optical purity of the amide recovered in the combined pH 6 extracts was assayed by chiral chromatography and found to be 95% (R)-ethyl 3-phenylacetamido-4-pentynoate. Optical purity of the amine recovered in the combined pH 8 extracts was assayed by chiral chromatography after derivatization with a-naphthoyl chloride and found to be 58% (S)-ethyl 3-amino-4-pentynoate.

EXAMPLE 3

Enzymatic Acylation added. After 5 minutes, immobilized penicillin G acylase (8 units) (Boehringer Mannheim) was added. The pH was adjusted to 6 using dilute sodium hydroxide. The reaction was stirred at room temperature for about 28 hours. The reaction mixture was extracted with ethyl acetate (3×25 mL) and the organic extracts combined and preserved. The immobilized enzyme was filtered off from aqueous phase using Whatman No.1 filter paper. The pH of the aqueous phase was adjusted to 8.0 using dilute sodium hydroxide, and extracted with ethyl acetate (25 mL×3). These extracts were combined with the preserved organic phase. Using acid base extraction known to those of ordinary skill in the art, the amine and amide were separated.

B) Phenyl acetic acid (20 grams) was suspended in 900 mL water. To this was added approximately 60 mL 2.5 N NaOH. To this solution was added 16 grams t-butyl 3-amino-5-trimethylsilyl-pent-4-ynoate (tosylate salt). Immobilized penicillin G acylase (40 grams, washed with water) was added and the suspension stirred at room temperature. After four days 65 mL 5% (w/v) $NaHCO_3$ was added and the suspension was extracted with ethyl acetate. The ethyl acetate extracts were extracted with dilute hydrochloric acid. After drying with $MgSO_4$ and evaporation, the ethyl acetate extracts gave 7.68 grams of the (R)-amide. The aqueous layers were neutralized with 5% $NaHCO_3$ and extracted with ethyl acetate. After drying the separated ethyl

Method A: R = Ethyl
Method B: R = H

A) Phosphate buffer (50 mL, 0.01 molar, pH 7.4) was added to 1,1-dimethylethyl 3-amino-S-(trimethylsilyl)-4-pentynoate hydrochloride (2 mmoles). The solution was stirred vigorously. Ethylphenyl acetate (2.5 mmoles) was acetate over $MgSO_4$ and evaporation, 2.82 grams of (S)-amine were recovered. Chiral HPLC indicated that the final product amine was 98.6% (S) stereoisomer and 1.4% (R) stereoisomer.

EXAMPLE 4

Enzymatic Deacylation

Racemic ethyl 3-(phenylacetamide)-4-Pentenoate (20 mg) was dissolved in acetonitrile (5 mL). Phosphate buffer (10 mL, 0.01 M prepared from 0.1 M phosphate buffer obtained from Sigma) was added and the reaction mixture was stirred. To this clear reaction mixture was added immobilized enzyme (50 mg (wet), Rohm-Pharma). The reaction flask was stoppered and the reaction mixture was stirred for 20 h at room temperature. The reaction mixture was filtered, and the residue was washed with acetonitrile (2×5 mL). The washings were mixed with the filtrate and concentrated to about 5 mL. This concentrate was extracted with boiling hexane (3×15 mL). The hexane extracts were mixed together, dried over sodium sulfate, filtered and evaporated to dryness. This dry material was then dissolved in isopropanol:hexane (4:6) and analyzed for the amides that formed. The chiral HPLC column gave a chromatogram indicating the S-amide to R-amide ratio as 97:3. The quantitative HPLC analysis accounts for 9 mg of the S-amide.

EXAMPLE 5

Enzymatic Deacylation

Racemic ethyl 3-(phenylacetamido)-5-(trimethylsilyl)-4-pentynoate (827 mg) was dissolved in a minimum amount methanol. Phosphate buffer (100 mL, 0.01 M, prepared from 0.1 M pH 7.24 solution obtained from Sigma) was added to the reaction mixture. The pH was 8.62. Using dilute sulfuric acid the pH was adjusted to 7.85. Under slow stirring, 134 mg of immobilized penicillin G acylase (immobilized on Eupergit PCT-600, Rohm-Pharma) was added. Sodium hydroxide (2.5 M) was used to maintain the pH at 7.85. The reaction was allowed to continue until 0.55 ml of base was consumed and then the reaction mixture was filtered. The filtrate was subjected to slow evaporation of methanol under reduced pressure. This resulted in precipitation of (S)-amide. 294 mg of amide was recovered from a first crop of material (39:58 R:S) and 174 mg of amide was recovered from a second crop (20:70 R:S). The material from the second crop also indicated desilylation.

EXAMPLE 6

Enzymatic Deacylation (BB)

Racemic 1,1-dimethylethyl-3-(phenylacetamido)-5-(trimethylsilyl)-4-pentynoate (750 mg) was suspended in phosphate buffer (150 mL, 0.01 M, prepared from 0.1 M pH 7.24 solution obtained from Sigma). The pH of the solution was adjusted between 7.8 to 8.0 using dilute sodium hydroxide. Under slow stirring, 100 units of immobilized penicillin G acylase (Boehringer-Mannheim) was added. Stirred at room temperature for 48 hours. Reaction mixture was extracted with ethyl acetate (75 mL×3). The organic extracts were combined, dried over sodium sulfate, filtered and evaporated to dryness to give the desired amide, (S)-1,1-dimethylethyl-3-(phenylacetamido)-5-(trimethylsilyl)-4-pentynoate. Immobilized enzyme was filtered off from aqueous phase using Whatman No.1 filter paper. The pH of the aqueous phase was adjusted to 8.0 using dilute sodium hydroxide, and extracted with ethyl acetate (75 mL×3). These extracts were combined, dried over sodium sulfate, filtered and evaporated to dryness to give the desired amine, (R)-1,1-dimethylethyl-3-amino-5-(trimethylsilyl)-4-pentynoate.

EXAMPLE 7

Enzymatic Deacylation

Racemic ethyl 3-(phenoxyacetamido)-5-(trimethylsilyl)-4-pentynoate (1g) was suspended in phosphate buffer (250 mL, 0.01 molar, prepared from 0.1 molar pH 7.24 solution obtained from sigma). The pH of the solution was adjusted 7.8 using dilute sodium hydroxide. Under slow stirring, 100 units of immobilized penicillin G acylase (Boehringer-Mannheim) was added. The reaction mixture was stirred at room temperature for 48 hours. The reaction mixture was extracted with ethyl acetate (75 mL×3). The organic extracts were combined, dried over sodium sulfate, filtered and evaporated to dryness to give the desired amide, (S)-ethyl-3-(phenoxyacetamido)-5-(trimethylsilyl)-4-pentynoate. The immobilized enzyme was filtered off from the aqueous phase using Whatman No.1 filter paper. The pH of the aqueous phase was adjusted to 8.0 using dilute sodium hydroxide, and extracted with ethyl acetate (75 mL×3). The extracts were combined, dried over sodium sulfate, filtered and evaporated to dryness to give the desired amine, (R)-ethyl-3-amino-5-(trimethylsilyl)-4-pentynoate.

EXAMPLE 8

Enzymatic Deacylation

Racemic ethyl 3-(phenylacetamido)-4-pentynoic acid (400 mg) was suspended in phosphate buffer (100 mL, 0.01 molar, prepared from 0.1 molar pH 7.24 solution obtained from sigma). The pH of the solution was adjusted between 8.0 to 8.2 using dilute sodium hydroxide. Under slow stirring, 100 units of immobilized penicillin G acylase (Boehringer-Mannheim) was added. The reaction mixture was stirred at room temperature for 48 hours, the pH was adjusted to 3.0, and then extracted with ethyl acetate (3×50 mL). The organic extracts were combined, dried over magnesium sulfate, filtered and evaporated to give the desired amide, (S)-ethyl-3-(phenylacetamido)-4-pentynoic acid.

Immobilized enzyme was filtered off from aqueous phase using Whatman No.1 filter paper. The pH of the aqueous phase was adjusted to 8 and extracted with ethyl acetate (50 mL×3). The extracts were combined, dried over magnesium sulfate, filtered and evaporated to give the desired amine, (R)-3-amino-4-pentynoic acid.

EXAMPLE 9

Enzymatic Phenylacylation Use of Penicillin G Acylase

R-amide

S-amine
Purity: > 99.4%
ee: > 99

The racemic amine hydrochloride (3 g) was placed in a 250 mL round bottom flask to which phosphate buffer (100 mL, 0.1 M) was added. The mixture was stirred to disperse the material. The pH of the medium was 6.41. Phenylacetic acid solution (1,7 mL, 6.5 mmoles, 0.65 equiv.) was added drop wise. Using dilute hydrochloric acid the pH was adjusted to 5.36. Immobilized penicillin C acylase (345 Units, Boheringer-Mannheim) was added and stirred at room temperature. After 120 hours, the reaction flask was cooled in an ice-bath.

Using hydrochloric acid (2N), pH was adjusted to 1.76. This reaction mixture was transferred to a separating funnel and extracted with ethyl acetate (50 mL×3). The organic phase was washed in the following order: 1) aqueous hydrochloric acid (pH 2; 100 mL×2), brine (100 mL), dilute potassium bicarbonate solution (100 mL×2), brine (100 mL), and dilute potassium bicarbonate solution (100 mL×2). The acidic aqueous phase was filtered on a Whatman No. 1 filter paper. Using acid base extraction as described in Example 1, amine and amides were separated. After isolation, 1.028 g of the desired (S)-amine was obtained in 99.4% chemical purity and 99% optical purity.

What is claimed is:

1. A method for preparing a chiral beta amino acid or its corresponding ester which comprises contacting a racemic beta amino acid or its corresponding ester, an acyl donor and Penicillin G acylase enzyme under conditions appropriate to stereoselectively acylate one enantiomer of the racemic beta amino acid to its corresponding N-acylated derivative and the opposite enantiomer of the beta amino acid remains substantially unreacted, thereby producing a chiral beta amino acid, wherein the racemic beta amino acid has the structure:

wherein $R^1$ comprises substituted or unsubstituted alkenyl or alkynyl, optionally substituted with alkyl, halogen, haloalkyl, cyano, hydroxy, aryl, fused aryl, nitro, alkyoxy, aryloxy, akylsulfonyl, arylsulfonyl, sulfonamide, thio, alkylthio, carboxyl derivatives, amino, and amido; and $R^2$ comprises hydrogen or unsubstituted alkyl and, in the case of the free acid, all pharmaceutically acceptable salts thereof.

2. A method for preparing an enantiomerically enriched beta amino acid or its corresponding ester which comprises contacting (i) a racemic beta amino acid having the structure:

wherein $R^1$ comprises substituted or unsubstituted alkenyl or alkynyl, optionally substituted with alkyl, halogen, haloalkyl, cyano, hydroxy, aryl, fused aryl, nitro, alkyoxy, aryloxy, akylsulfonyl, arylsulfonyl, sulfonamide, thio, alkylthio, carboxyl derivatives, amino, and amido; and $R^2$ comprises hydrogen or unsubstituted alkyl and, in the case of the free acid, all pharmaceutically acceptable salts thereof, or its corresponding ester, (ii) an acyl donor and (iii) Penicillin acylase enzyme under conditions appropriate to stereoselectively acylate one enantiomer of the racemic beta amino acid to its corresponding N-acylated amino acid derivative, whereby the opposite enantiomer of the beta amino acid is retained in substantially enantiomerically enriched form, and separating the N-acylated amino acid derivative from the retained beta amino acid.

3. A method for preparing a chiral beta amino acid or its corresponding ester which comprises:
(a) dissolving a racemic beta amino acid or its corresponding ester in phenyl acetic acid to form a salt of the racemic beta amino acid and phenylacetic acid; wherein in the racemic beta amino acid has the structure:

wherein $R^1$ comprises substituted or unsubstituted alkenyl or alkynyl, optionally substituted with alkyl, halogen, haloalkyl, cyano, hydroxy, aryl, fused aryl, nitro, alkyoxy, aryloxy, akylsulfonyl, arylsulfonyl, sulfonamide, thio, alkylthio, carboxyl derivatives, amino, and amido; and $R^2$ comprises hydrogen or unsubstituted alkyl and, in the case of the free acid, all pharmaceutically acceptable salts thereof;
(b) dissolving the salt formed in (a) with an aqueous solvent;
(c) adding Penicillin G acylase enzyme to the aqueous solution (b) under conditions appropriate to stereoselectively acylate one enantiomer of the racemic beta amino acid to its corresponding N-acylated derivative and the opposite enantiomer of the beta amino acid remains substantially unreacted.

4. The method of claim 1 or 2 wherein the acyl donor has the structure:

wherein $R^3$ comprises substituted or unsubstituted phenyl, phenoxy, amino, phenyl glyconyl, 4-methylphenyl, 4-methoxy phenyl, p-nitro phenyl, 2-pyridyl, 3 pyridyl and 4-pyridyl and $R^4$ comprises hydroxy; alkoxy, alkyl; alkenyl; alkynyl; haloalkyl; aryl; arylalkyl; sugars and steroids.

5. The method of claim 4 wherein $R^3$ is alkoxy chosen from the group consisting of ethoxy, methoxy, butoxy, 2-chloroethoxy, trichloroethoxy, trifluoroethoxy, cyanomethoxy, vinyloxy, substituted vinyloxy, acetyloxy, and phenacetyloxy.

6. The method of claim 4 wherein the acyl donor is chosen from the group consisting of methyl phenoxyacetate, methyl phenylacetate and phenylacetic acid.

7. The method of claim 6 wherein the acyl donor is phenyl acetic acid.

8. The method of claim 1, 2, or 3 wherein the Penicillin G acylase enzyme is derived from microorganisms chosen from the genera Acetobacter, Xanthomonas, Mycoplana, Protaminobacter, Aeromonas, Pseudomonas, Flavobacterium, Aphanocladium, and Cephalosporium.

9. The method of claim 1, 2, or 3 wherein the enzyme is immobilized on a solid support.

10. The method of claim 1 or 2 wherein the ratio of enzyme to substrate to acyl donor is between about 1500 u:25 g:13 g and about 7000 u:50 g:38 g.

11. The method of claim 10 wherein the ratio of enzyme to substrate to acyl donor is 3750 u:37.5 g:24.5 g.

12. The method of claim 1 or 2 wherein the conditions appropriate to stereoselectively acylate one enantiomer of the racemic beta amino acid comprise aqueous conditions.

13. The method of claim 1 or 2 wherein the conditions appropriate to stereoselectively acylate one enantiomer of the racemic beta amino acid comprise organic conditions.

14. The method of claim 13 wherein the organic conditions comprise addition of an organic cosolvent chosen from the group consisting of acetone, tetrahydrofuran, dimethylformamide, acetonitrile, isopropanol, methanol, and toluene.

15. The method of claim 14 wherein the organic cosolvent is present in an amount greater than 0 up to about 30% (v/v).

16. The method of claim 15 wherein the organic cosolvent is present in an amount of about 5% (v/v).

17. The method of claim 1, 2 or 3 wherein the chiral beta amino acid is chosen from the group consisting of ethyl 3-amino-5-(trimethylsilyl)-4-pentynoate, ethyl 3-amino-4-pentynoate, 1,1-dimethylethyl-3-amino-5-(trimethylsilyl)-4-pentynoate, and 1,1-dimethylethyl 3-amino-5-(trimethylsilyl)-4-pentynoate.

* * * * *

UNITED STATES PATENT AND TRADEMARK OFFICE
CERTIFICATE OF CORRECTION

PATENT NO. : 6,214,609 B1  
DATED : April 10, 2001  
INVENTOR(S) : Bryan H. Landis et al.

It is certified that error appears in the above-identified patent and that said Letters Patent is hereby corrected as shown below:

<u>Title page, Item [54] and Column 1, Line 1,</u>
Title, "METHOD AND APPARATUS FOR PREPARATION OF CHIRAL BETA AMINO ACIDS USING PENICILLIN G ACYLASE", should read
-- METHOD AND APPARATUS FOR PREPARATION OF CHIRAL BETA AMINO ACIDS --.

<u>Column 9,</u>
Line 10, "50xH" should read -- 50x H --.

<u>Column 14,</u>
Line 28, "48%." should read -- 48% --.

<u>Column 23,</u>
Line 10, "in" should be deleted; and
Line 29, "solvent;" should read -- solvent; and --.

Signed and Sealed this

Twentieth Day of August, 2002

*Attest:*

*Attesting Officer*

JAMES E. ROGAN
*Director of the United States Patent and Trademark Office*